United States Patent [19]
Ueda

[11] Patent Number: 5,554,024
[45] Date of Patent: Sep. 10, 1996

[54] DENTAL IMPRESSION PAPER TRAY

[75] Inventor: Masahiko Ueda, Kaizuka, Japan

[73] Assignee: Taihei Chemical Industrial Co., Ltd., Osaka, Japan

[21] Appl. No.: 282,742

[22] Filed: Jul. 29, 1994

[30]     Foreign Application Priority Data

Jul. 30, 1993  [JP]  Japan ................................ 5-190145

[51] Int. Cl.⁶ .................................................. A61C 9/00
[52] U.S. Cl. ................................ 433/37; 433/46
[58] Field of Search ............................. 433/37, 41, 42, 433/43, 45, 46, 68, 70, 71, 214

[56]            References Cited

U.S. PATENT DOCUMENTS

| | | | |
|---|---|---|---|
| 1,099,101 | 6/1914 | Robertson | 433/46 |
| 1,113,090 | 10/1914 | Bell | 433/46 |
| 1,374,183 | 4/1921 | Bridges | 433/46 |
| 1,461,209 | 7/1923 | Bridges | 433/46 |
| 1,728,137 | 9/1929 | Riddle | 433/46 |
| 2,841,311 | 6/1959 | Wood | 433/37 |
| 2,924,011 | 2/1960 | McAdoo | 433/46 |
| 3,247,844 | 4/1966 | Berghash | 433/37 X |

FOREIGN PATENT DOCUMENTS

4-317648   11/1992   Japan .

*Primary Examiner*—Nicholas D. Lucchesi
*Attorney, Agent, or Firm*—Oblon, Spivak, McClelland, Maier, & Neustadt, P.C.

[57]              ABSTRACT

A dental impression paper tray comprising a material mainly composed of pulp which is compressed molded to a dental impression tray shape having a thickness of 0.5–10 mm. Minute concavities/convexities may be formed at least on the inner surface of the paper dental impression tray. Paraffin wax may be dispersingly included in the tray or coated on the surface of the tray. A handle of the tray may be integrally attached to a dish portion by insertion or adhesion. Since the tray is made of paper and is less expensive, it can be domestically disposed with an incinerator as a disposal tray. Further, the tray having the minute concavities/convexities has an increased holding force to an impression material. The tray to or in which paraffin wax is coated or contained has increased water resistance.

6 Claims, 6 Drawing Sheets

DENTAL IMPRESSION PAPER TRAY

BACKGROUND OF THE INVENTION

1. Field of the Invention

The present invention relates to a dental impression paper tray used for a purpose of an impression-taking in a mouth in a dental treatment.

2. Description of the Related Art

When prostheses such as dentures and the like are made in a dental treatment, an impression in the mouth of a patient is collected by use of an impression tray.

Conventional dental impression trays are generally made of metal or plastic. Since dental impression trays are expensive, they are cleaned after having been used so that they can be used repeatedly.

However, when impression trays are used repeatedly, they give a feeling of uneasiness and a sense of uncleanliness to patients because they may be broken or corroded in a cleaning operation as well as there is a problem of infection such as AIDS caused by HIV. Thus, there have been desired disposable impression trays.

To satisfy this desire, there has been developed a disposable impression tray as disclosed in Japanese Patent Laid-open No. HEI 4-317648 (1992). This disposable tray is composed of a thermoplastic resin with reinforced fibers.

Nevertheless, since the conventional disposable dental impression tray contains the resin, when the tray is intended to be disposed by incineration as a generally used waste disposal method, a high thermal energy is needed and further a toxic gas is generated depending upon a type of the resin, reinforced fibers and other additives. As a result, a problem of air pollution arises and causes general personal dentist clinics to find it difficult to dispose the tray by themselves.

SUMMARY OF THE INVENTION

An object of the present invention is to provide a dental impression paper tray which has a sufficient strength and water resistance and a good holding force thereof to an impression material, can be easily disposed by incineration, does not cause a problem of dumping of polluted waste, and is less expensive. Another object of the present invention is to provide a dental impression paper tray having an improved mechanical strength. Still another object of the present invention is to provide a dental impression paper tray having an increased holding force to an impression material. A further object of the present invention is to provide a dental impression paper tray having improved water resistance so that the tray keeps a strength even if it is exposed to water. A still further object of the present invention is to provide a dental impression paper tray which can be accomodated in a small space.

A dental impression paper tray including a dish portion and a handle portion according to the present invention comprises a material mainly composed of pulp and is compressed molded to a dental impression tray shape having a thickness of 0.5–10 mm. Preferably, concave portions or convex portions are formed on at least the inner surface of the dental impression paper tray. Preferably, paraffin wax is dispersingly included in the dental impression paper tray or coated on the surface thereof. Further, a handle portion and a dish portion may be integrally molded to form a tray, or a handle portion and a dish portion may be made individually and attached together by insertion or adhesion.

DESCRIPTION OF THE PREFERRED EMBODIMENTS

Figure 1A:
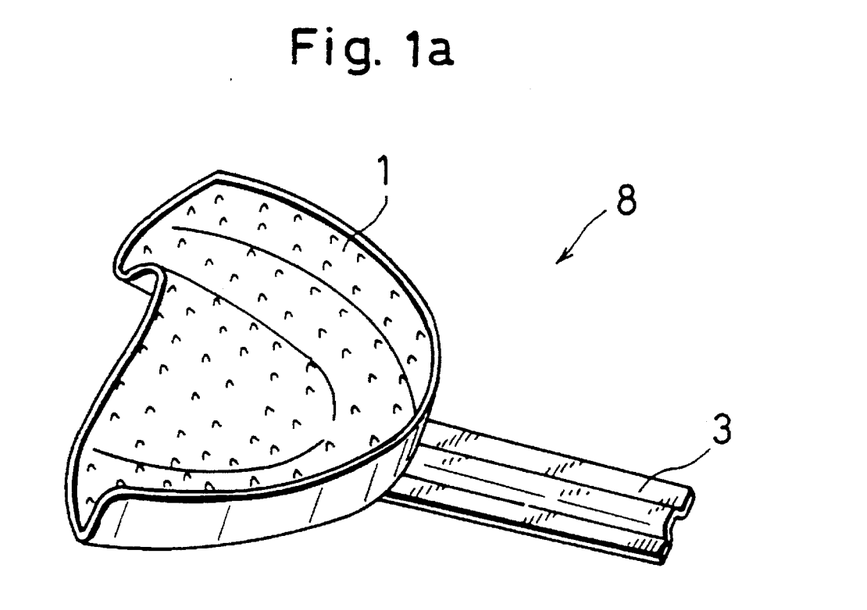
FIGS. 1a and 1b are perspective views showing a dental impression paper tray according to a first embodiment of the present invention.
Figure 1B:
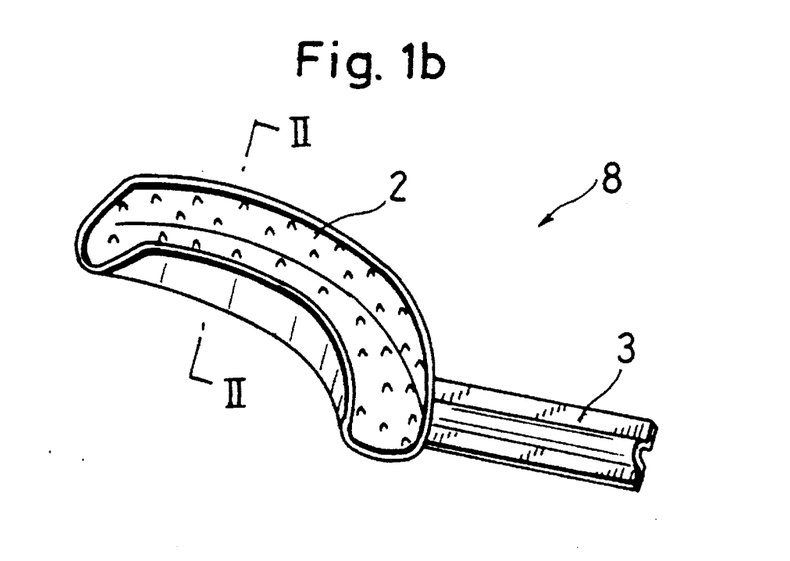

FIGS. 1a and 1b are perspective views showing a dental impression paper tray 8 according to a first embodiment of the present invention, wherein FIG. 1a shows a tray for the whole jaw and FIG. 1b shows a tray for a partial jaw. In FIG. 1a and 1b, numerals 1 and 2 denote a dish portion of the tray and numeral 3 denotes a handle of the tray.

Figure 2A:
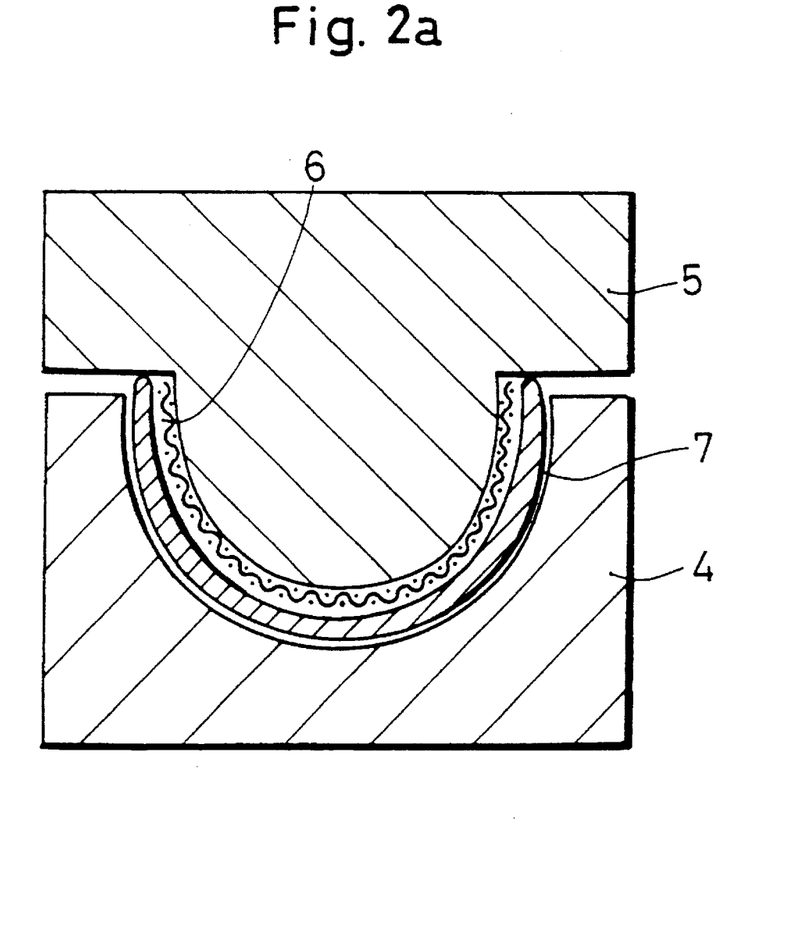
FIGS. 2a and 2b are cross sectional views showing a process for manufacturing a dental impression paper tray according to the present invention by way of example.

FIGS. 2a and 2b are views showing a process for manufacturing a dental impression paper tray according to the present invention, and is viewed from the cross section taken along the line II—II of FIG. 1b. In FIG. 2a, numeral 4 denotes a female mold of a pair of impression tray mold and numeral 5 denotes a male mold thereof. Numeral 6 denotes a net disposed in the inner wall of the male mold 5, and numeral 7 denotes a roughly molded original tray.

Next, a manufacturing method of the dental impression paper tray of the present invention will be described. Note, in this embodiment, the tray was made by use of a pulp mold molding machine (made by Uthui Co.).

First, a pulp material is preliminarily pressed for rough dehydration as well as the shape thereof is adjusted so that the preformed tray 7 is obtained. The original tray 7 is disposed between the molding mold composed of the male mold 5 provided with the net 6 and the female mold 4 (FIG. 2a). Next, the female mold 4 and the male mold 5 are vertically clamped while being heated and, by means of pressing and drying the original tray 7, the dish portion 2 is molded. With this arrangement, minute concavities/convexities are formed to the inner wall of the dish portion 2 by insertion of the net 6 (FIG. 2b).

Figure 2B:
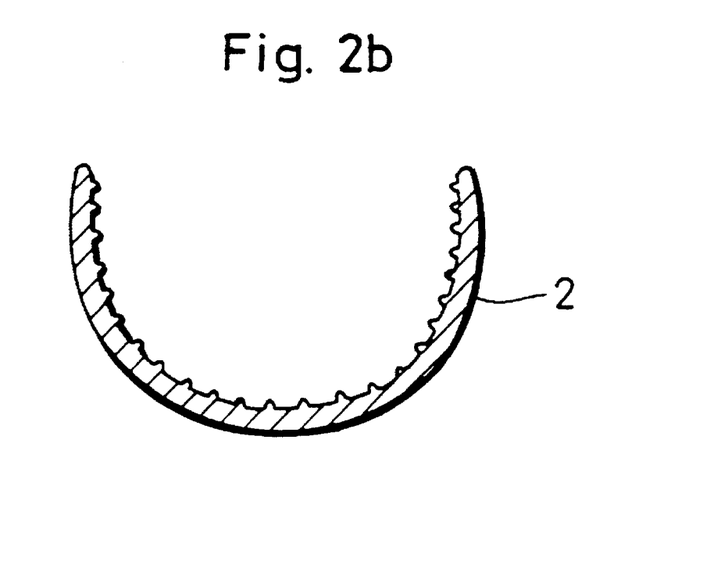

Then, a tray 8 is assembled by attaching the handle 3 made by a similar method to the main dish 2 using an adhesive, pins or the like (FIG. 2b).

The tray 8 is finished by being coated with paraffin wax emulsion SPW-116H (made by Arakawa Kagaku Kogyo Co.) and dried at 105° C. for one hour (FIG. 1a, 1b).

A function of the dental impression paper tray of the present invention will be described as follows.

Since the dental impression paper tray of the present invention is compressed molded to a high density, it has a sufficient strength and improved water resistance. The compressed density (measured at the flat portion of the tray) is 0.5 g/cm$^3$ or more, preferably 0.7 g/cm$^3$ or more, and more preferably 0.8 g/cm$^3$ or more. The tray of the present invention has a thickness of 0.5–10 mm. This is because when the thickness is less than 0.5 mm, the tray may be broken because it has an insufficient strength, whereas when the thickness exceeds 10 mm, the tray, when it is inserted into a mouth, is difficult to take an impression, and since a thickness of an impression material is made relatively thin, an impression cannot be accurately taken. A thickness of 1–5 mm is more preferable to take an impression more accurately and more simply.

Various types of impression materials such as alginate impression material, silicone rubber impression material and the like can be used, and these impression materials have good wettability with the pulp used as a material of the tray and are strongly adhered to the tray.

The convex portions in the minute concavities/convexities formed to the tray of the present invention particularly exhibits a function as a reinforcing rib to the dish portion 2. It has been confirmed, however, that when the dish portion 2 has a sufficient thickness, it exhibits a sufficient mechanical strength without the formation of the concave/convex portions. Therefore, even if a large external force is applied to the tray when it is taken out from a mouth in the collection of an impression, the tray is hardly deformed. Note, although minute concavities/convexities are not formed to the handle 3 in the above embodiment, it suffices for a person embodying the present invention to determine whether the minute concavities/convexities is to be formed to the handle 3 in consideration of a thickness thereof.

Further, as the minute concavities/convexities are provided on the inner surface of the dish portion, when an impression is being taken, the impression material which enters the minute concavities/convexities is firmly fixed to the dish portion. As a result, an anchor effect or an increase of a contact area, and the like are obtained. Note, when an impression is taken, an adhesive may be coated on the surface of the dish portion 2 to more strongly hold the impression material.

More specifically, although a force for strongly holding an impression material and a high mechanical strength are required to the impression tray to take a precise impression for dental use, the tray of the present invention holds the impression material well and has a sufficient strength as described above.

As a surface area of the tray is increased by the provision of the minute concavities/convexities on the surface thereof, the tray can be dried well when it is manufactured.

Since the dish portion 2 and the handle 3 of the present invention are sterilized by being heated when clamped, they are sanitary. Further, the tray 8 may be sterilized by being irradiated by ultraviolet rays or by being exposed to a ethylene oxide gas (EOG) and the like after the completion of the tray 8. When the tray is packed in a sterilized state just after manufacturing, it is kept in a sanitary state and can be used as it is, when necessary without the need of sterilizing treatment.

Generally, a used tray can be most easily disposed by incineration. Since the dental impression tray of the present invention is composed of a paper making material called pulp mold, the tray does not generate a toxic gas even if it is disposed by incineration. Further, since the tray need not be disposed at a high combustion temperature as in the case of a resin, it can be domestically disposed by a domestic incinerator and thus no problem is caused in a waste disposal. The dental impression tray according to the present invention may be sometimes coated with or contains paraffin wax. In this case, the paraffin wax does not also generate a toxic gas in incineration, and the wax need not be disposed at a high combustion temperature, it can be domestically disposed easily.

In addition, since the dental impression tray is composed of paper, the tray can be easily processed by being cut with scissors, knife and the like. Therefore, even if many types of trays are not prepared, a tray suitable for the mouth of each patient can be fitted by use of a few types of trays.

Further, a manufacturing cost of the dental impression tray of the present invention is not increased because the tray can be made by a simple manufacturing method of compressed hardening and further a material of the tray is less expensive, and therefore, the tray is suitable as a disposable tray. Since the tray can be used as a disposable tray because of the reason as described above, a time-consuming job such as cleaning, sterilization and the like which is conventionally required to reuse a tray is not necessary and there is no anxiety of contagion, and thus the dental impression tray is sanitary.

Next, a test of mechanical properties of the dental impression tray of the present invention carried out by using the flat portion thereof will be described.

A tensile strength, density and hygroscopic property of the trays of the present invention to which wax was coated and to which wax was not coated were examined.

The tensile strength was tested according to JIS K-6550.

The test to determine the density was carried out by using test pieces of 25±2 mm long, 15±2 mm wide and 1±0.2 mm thick. The test pieces were held in a thermo-hygrostat condition of temperature of 24±2° C. and relative humidity of 50±10% for 24 hours or longer, and then the weights of the prepared test pieces were measured (up to a level of 0.1 mg). The measured weights were divided by the volumes of the test pieces (down to the second decimal place), and thereby the density can be obtained.

The test to determine the hygroscopic property was carried out by using test pieces being the same dimensions as those used in the above density test. The test pieces were dried at 105° C. for one hour and then held in the condition of thermo-hygrostat of temperature of 35±2° C. and a relative humidity of 95% or higher, and the state of the test pieces were checked visually and by touch after the elapse of time of one hour and 24 hours.

Table 1 shows a result of the tests.

TABLE 1

| | Tensile Strength (Kg/cm) | Density (g/cm) | Hygroscopic Property | |
|---|---|---|---|---|
| | | | After 1 Hour | After 24 Hours |
| Wax not coated | 268 | 0.82 | Not changed | Softened |
| Wax coated | 287 | 0.84 | Not changed | Not changed |

It can be found from the result of the tests shown in Table 1 that even the tray which is not coated with wax exhibits a sufficient strength and water resistance. Therefore, the trays of the present invention have a function as a dental impression tray. The tray coated with wax has mechanical properties which are more increased as compared with the tray not coated with wax.

Other embodiments of the dental impression paper tray according to the present invention will be described.

Although the first embodiment forms the minute concavities/convexities on the inner surface of the dish portion 2 by disposing the net 6 on the molding surface of the male mold 5, the method of forming the minute concavities/convexities is not limited to the above method using a net but the minute concavities/convexities may be made by using the male mold 5 having minute concavities/convexities on the molding surface thereof. In this case, a tray having minute concavity/convexity corresponding to the minute convexity/concavities of the male mold is made.

Figure 3A:
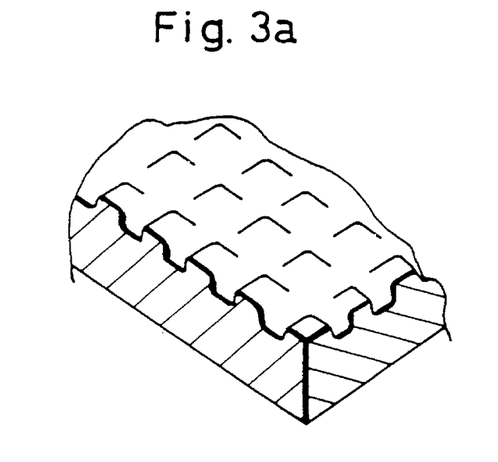
FIGS. 3a, 3b and 3c are perspective views partly in cross section showing a minute concave/convex configuration of a dental impression paper tray according to second, third and fourth embodiments of the present invention.
Figure 3B:
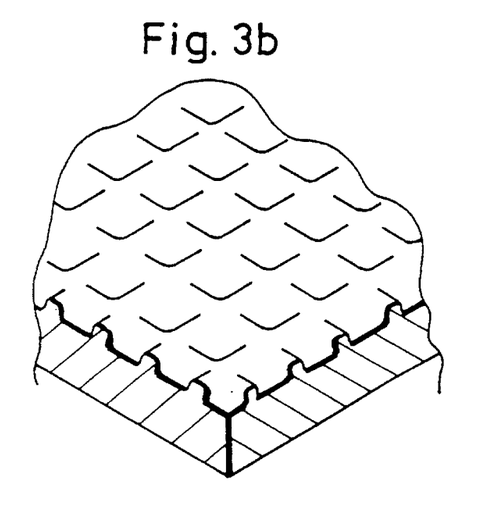
Figure 3C:
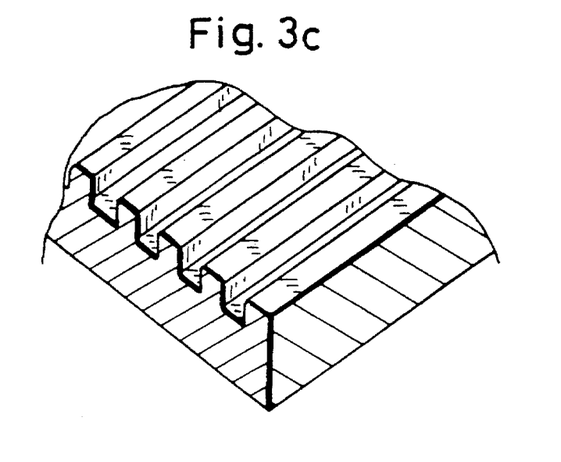

As shown, for example, in the perspective view in partially cross section: FIGS. 3a, 3b and 3c the minute concave/convex configuration of the tray may be formed to various types of a dot shape (second and third embodiments : FIG. 3a, 3b a line shape (fourth embodiment of FIG. 3c), and minute convexity (minute concavity) having various configurations such as a band shape, a zigzag shape and the like. These configurations can be formed by making the minute concavities/convexities of the inner wall of the male mold 5 any configuration.

Figure 4:
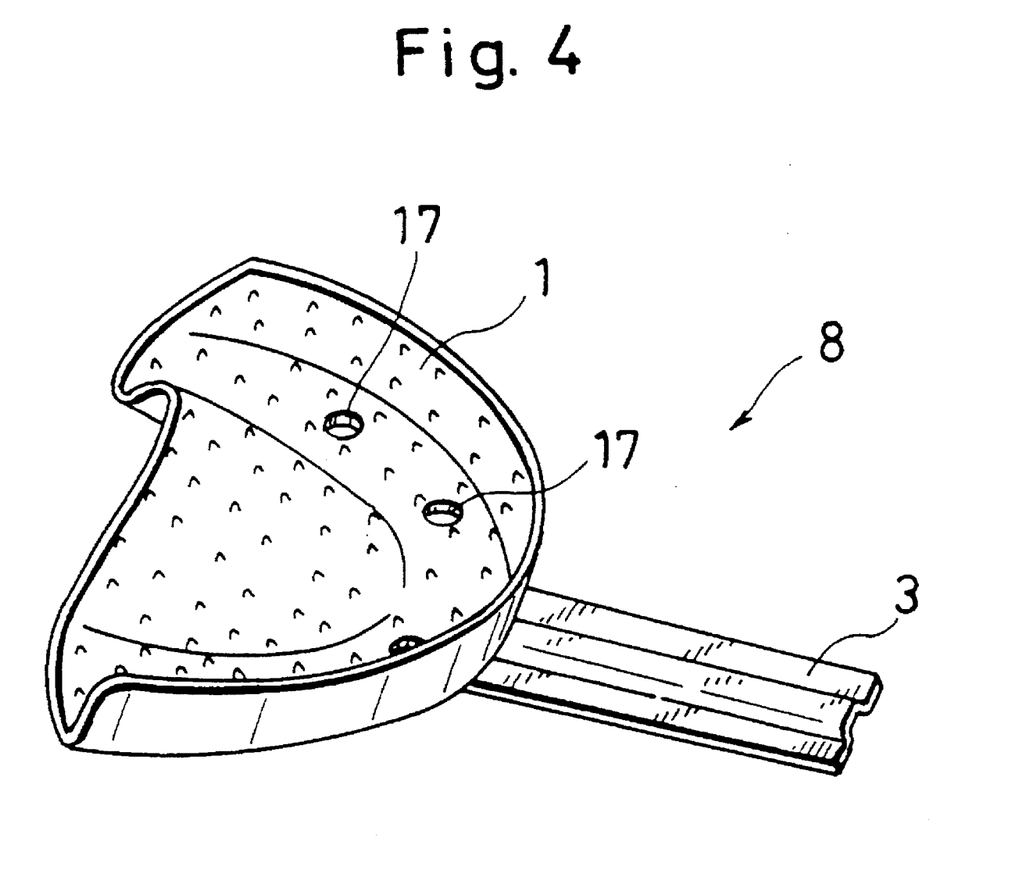
FIG. 4 is a perspective view showing a dental impression paper tray according to a fifth embodiment of the present invention.

Further, as shown in FIG. 4, flow-out holes 17 may be defined at several positions of the dish portion 2 as necessary to flow out an excessive impression material when an impression is collected. The impression material is more completely integrated with the dish portion by the impression material entering into the flow-out holes 17 so that the impression material can be more firmly held (fifth embodiment).

Although the dish portion 2 and the handle 3 are separately made and then bonded to each other by an adhesive or pins in the first embodiment, the handle 3 may be detachably inserted into the dish portion as described below by employing an insertion type. Otherwise, the dish portion and the handle may be Integrally molded.

Figure 5A:
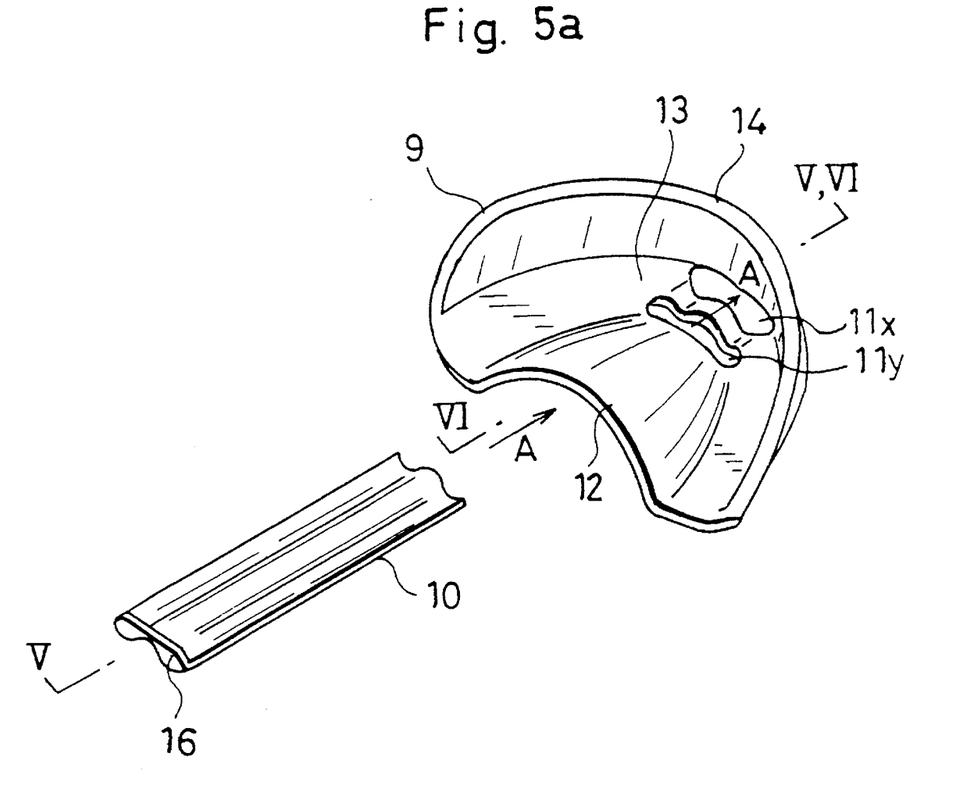
FIGS. 5a and 5b are views showing a dental impression paper tray according to sixth and seventh embodiments of the present invention.
Figure 5B:
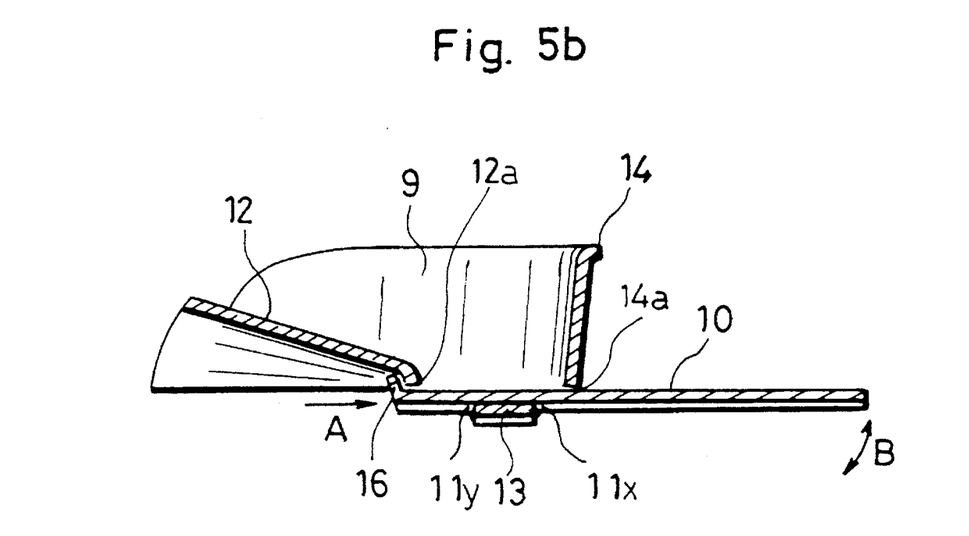

FIG. 5a and 5b shows an insertion type dental impression paper tray according to embodiments 6 and 7, wherein FIG. 5a shows a perspective view of the tray before a handle is inserted into a dish portion and FIG. 5b is a cross sectional view of the tray showing that the handle is inserted into the dish portion. Note, the cross section of FIG. 5b is taken along the line V—V of FIG. 5a. As shown in FIG. 5a and 5b, the dish portion 9 is deepened from a plate portion 12 corresponding to the bottom of an upper jaw to a tooth-shape recessed portion 13 drawing a gradual curve and steeply rises therefrom toward a tooth-shape edge portion 14.

The handle 10 is attached to the dish portion 9 by inserting the handle 10 into insertion holes 11x, 11y defined in the vicinity of the tooth-shape recessed portion 13 in the direction of an arrow A. A hook 16 is provided at an end of the handle 10 and the handle 10 is fixed to the dish portion 9 by hooking the hook 16 to the edge of on the plate portion 12 side of the insertion hole 11y.

Even if a force is applied to the thus fixed tray in the direction of an arrow B when an impression is collected, the dish portion 9 and handle 10 are rigidly integrated with each other by being supported by the edge portion 14a around the periphery of the insertion hole 11x, the edge portion 12a around the periphery of the insertion hole 11y and the recessed portion 13.

Figure 6:
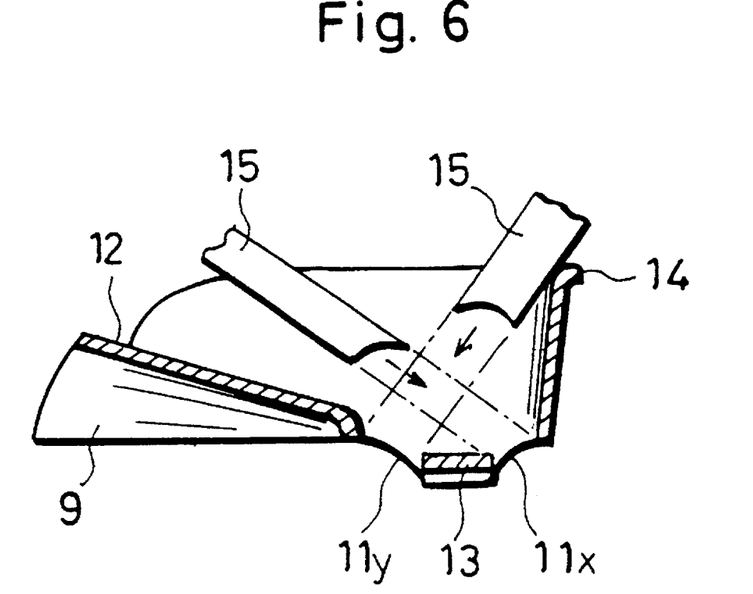
FIG. 6 is a cross sectional view showing a method of forming an inserting hole in the sixth embodiment of the present invention.
Figure 7:
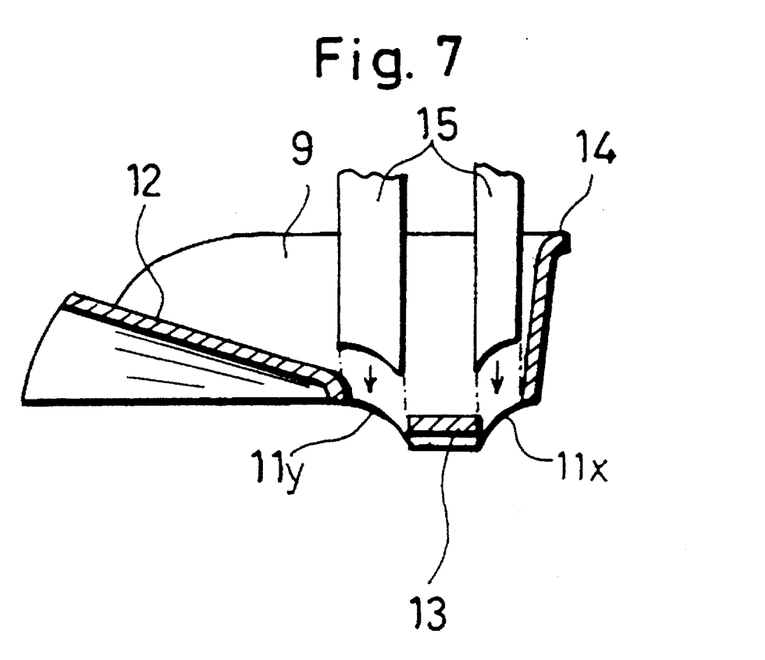
FIG. 7 is a cross sectional view showing a method of forming an inserting hole in the seventh embodiment of the present invention.

FIG. 6 and FIG. 7 are cross sectional views showing a method of forming the insertion holes 11x and 11y of the dish portion 9 and the cross section of the dish portion 9 is taken along the line VI—VI shown in FIG. 5a.

A method of forming the insertion holes 11x and 11y includes a method of blanking out the hole by blanking blades 15 from an oblique lateral direction as shown in FIG. 6 (hereinafter, referred to as a laterally blanking method: the sixth embodiment) and another method of blanking out the hole from a direction perpendicular (upwardly or downward) to a direction along which the handle 10 is inserted (hereinafter, referred to as an upwardly blanking method: the seventh embodiment) as shown in FIG. 7.

The size of the insertion holes 11x and 11y can be minimized in the case of the laterally blanking method (FIG. 6) because blanking can be carried out at the side wall of the recessed portion 13 which is corresponding to the tooth shape. Thus, the handle 10 can be firmly inserted.

Although the laterally blanking method needs two additional blanking processes independently of the compressed molding process, the upwardly blanking method (FIG. 7) can blank out the insertion holes 11x and 11y in a single blanking process after the preformed tray has been clamped in the process for making the dish portion 9 (refer to FIG. 2a) and thus the number of the processes can be reduced.

In the case of the insertion type paper dental impression tray, the tray main bodies 9 and the handles 10 can be separately stored and transported and thus a space for accommodating them can be saved.

When the dish portion 9 and the handle 10 are separately provided as described above, a user inserts the handle 10 into the dish portion 9 in use. Further, when the handle 10 is pulled out in the direction opposite to the direction of the arrow A, the handle 10 can be simply removed from the dish portion 9.

A pulp material used for the present invention may not be only virgin pulp but also recycled pulp made of used paper, and even in the case that the recycled pulp is used, cleanness is kept by the aforesaid sterilization. The dental impression tray can be made at a much less expensive cost when the used paper material is utilized.

Further, a paper force increasing agent such as starch, polyacrylamide etc. may be added to improve paper quality, and the addition of paraffin wax emulsion as in the case of the preferred embodiments of the present invention is particularly effective because water resistance is improved.

Paraffin wax coated on the surface of the tray may be impregnated into the tray by coating. Paraffin wax may be included in the tray by dispersingly containing it in a pulp material. In these cases, an effect of improving water resistance can be also exhibited.

Japanese Patent Application No. HEI 5-190145 filed Jul. 30, 1993 is herein incorporated by reference.

What is claimed is:

1. A dental impression paper tray comprising:
   a dish portion and a handle portion, wherein both said dish portion and said handle portion are substantially composed of pulp, which is compressed molded into a dental impression tray shape having a thickness of 0.5 mm–10 mm; wherein:
   said dish portion comprises a plate portion and a tooth shaped recessed portion, said dish portion further comprising first and second insertion holes positioned at said tooth shaped recessed portion;
   one end of said handle portion comprises a hook; and
   said handle portion is removably attached to said dish portion by slidably inserting said handle portion through said first and second insertion holes such that said hook on said handle portion hooks an edge of said plate portion which is adjacent to one of said first and second insertion holes.

2. A dental impression paper tray according to claim 1, wherein minute concavities and minute convexities are formed at least on an inner surface of said dental impression paper tray.

3. A dental impression paper tray according to claim 1, wherein paraffin wax is dispersingly included in said tray.

4. A dental impression paper tray according to claim 1, wherein paraffin wax is coated on a surface of said tray.

5. A dental impression paper tray according to claim 1, wherein said dish portion comprises flow-out holes for permitting an outflow of excessive impression material from said dish portion.

6. A dental impression paper tray according to claim 1, wherein said handle portion has a wave shape.

\* \* \* \* \*